United States Patent

Boyce et al.

[11] Patent Number: 5,981,814
[45] Date of Patent: *Nov. 9, 1999

[54] VAPOR PHASE PROCESS FOR PREPARING FLUORINATED ALIPHATIC COMPOUNDS

[75] Inventors: C. Bradford Boyce, Baton Rouge; Randolph K. Belter, Zachary, both of La.

[73] Assignee: LaRoche Industries Inc., Atlanta, Ga.

[*] Notice: This patent is subject to a terminal disclaimer.

[21] Appl. No.: 09/046,023

[22] Filed: Mar. 23, 1998

[51] Int. Cl.$^6$ ...................................................... C07C 17/08
[52] U.S. Cl. ........................... 570/167; 570/166; 570/168; 570/169
[58] Field of Search ..................................... 570/166, 167, 570/168, 169

[56] References Cited

U.S. PATENT DOCUMENTS 5,619,819  4/1997  Boyce et al. ............................. 570/167

*Primary Examiner*—Elli Peselev
*Attorney, Agent, or Firm*—Richard J. Hammond

[57] ABSTRACT

A process is disclosed for the preparation of a fluorinated aliphatic hydrocarbon having the formula $$CH_aF_{3-a}\text{—}CH_2\text{—}CH_bF_{3-b}$$

wherein a is 0 or the integer 1 or 2 and b is 0 or the integer 1, 2 or 3. The reaction occurs in the vapor phase. A chlorofluoro olefin of the formula $$CH_cCl_{2-c}\text{=}CH\text{—}CH_dF_{3-d}$$

wherein c is 0 or the integer 1 or 2, and d is 0 or the integer 1 or 2 is treated in the vapor phase with hydrogen fluoride. This treating is catalyzed with a compound that is a metal oxide, a metal halide or a mixture thereof. The metallic part of such compound is selected from a metal in Group IIIa, IIIb, IVa, Va, IVb, Vb, VIa, VIb, VIIb and VIII of the Periodic Table of the Elements. The treating is carried out for a time sufficient to form the desired fluorinated aliphatic hydrocarbon which is subsequently recovered from the vapor phase reaction.

The process is particularly suitable for the preparation of 1,1,1,3,3-pentafluoropropane.

10 Claims, No Drawings

VAPOR PHASE PROCESS FOR PREPARING FLUORINATED ALIPHATIC COMPOUNDS

FIELD OF INVENTION

This invention relates to a process for preparing aliphatic compounds substituted with multiple fluorine atoms. In particular, this invention relates to the discovery that a highly fluorinated aliphatic hydrocarbon can be prepared in high yield by a process comprising treating a chlorofluoro olefin with hydrogen fluoride in the vapor phase in the presence of a catalyst that is a metal oxide, metal halide or mixture thereof for a time sufficient to form said highly fluorinated aliphatic hydrocarbon.

BACKGROUND OF THE INVENTION

Chlorofluorocarbons (CFC's) are widely used in refrigerant compositions, propellants and cooling fluids as well as blowing agents, solvents and rinse agents. Their replacement with environmentally acceptable alternatives has produced an abundance of compounds meeting one or more of these needs. The most acceptable replacement compounds are those having little or no chlorine, since it is generally accepted that chlorinated aliphatics lead to unacceptable reactive chlorine-containing radicals when present in the upper atmosphere. These radicals are thought to react with the ozone in the stratosphere depleting it to dangerously low levels.

One of the more promising alternatives to CFC's are aliphatic compounds where chlorine has been replaced with fluorine. These materials are known as hydrofluorocarbons (HFC's). Typical HFC's have atmospheric lifetimes and global warming potentials that are a fraction of their chlorinated analogs. Fortunately, many of their other physical properties (low flammability and toxicity, sufficient volatility, etc.) are identical or similar to the CFC's. Accordingly, they are attractive replacements for the chlorinated molecules.

In processes for preparing HFC's, a usual starting material is the chlorinated analog of the desired fully fluorinated compound. Thus, U.S. Pat. No. 2,787,646 discloses that $SbF_3Cl_2$ and \or $SbF_3$ are useful for converting compounds of the formula $CMZ_2CX=CHY$, for example 3,3,3-trichloroprop-1-ene or 1,1,3-trichloroprop-1-ene to compounds of the formula $CF_3CX=CHY$, for example 3,3,3-trifluoroprop-1-ene.

U.S. Pat. No. 2,549,580 discloses the conversion of 1,1-dichloroprop-1-ene to 1,1,1-trifluoropropane by means of HF at 120° C. and 800 psi pressure.

U.S. Pat. No. 5,616,819 discloses a two step process for the preparation of fully fluorinated aliphatic hydrocarbons in which hydrogen fluoride is reacted with a chlorofluoro olefin in the presence of a catalyst for a time and at a temperature sufficient to form said fully fluorinated aliphatic hydrocarbon.

The preparation of 1-chloro-1,1,3,3,3-pentafluoropropane and of 1,1,1,3,3,3-hexafluoropropane from 1,1,1,3,3,3-hexachloropropane in the liquid phase is described in EPO Publication No. 0 522 639 A1. While the preferred catalyst for the reaction is noted to be $SbCl_5$, other catalysts disclosed are those metal chlorides, fluorides, and chloride fluorides of Group IIIa, IVa, IVb, Va, Vb and VIb of The Periodic Table of the Elements.

Compounds such as 1,1,1,3,3,3-hexafluoropropane are prepared by the coupling of two chlorine containing reactants, i.e., 1,1,1-trichloro-2,2,2-trifluoroethane and dichlorodifluoromethane, in the presence of hydrogen and a first catalyst to form an olefin, i.e.,1,1,1,3,3-pentafluoro-2-chloroprop-2-ene and then hydrogenating the olefin in the presence of a second catalyst. See WO 95/05353.

SUMMARY

The process of the present invention to prepare a fluorinated aliphatic hydrocarbon utilizes an olefinic starting material of the formula

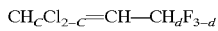

wherein c is 0 or the integer 1 and d is 0 or the integer 1 or 2. This olefinic starting material (a chlorofluoro olefin)is reacted in the vapor phase with hydrogen fluoride in the presence of a catalyst to form the desired fluorinated aliphatic hydrocarbon, i.e., a compound of the formula

The fluorinated aliphatic hydrocarbon is subsequently separated from the vapor phase reactants and recovered

DESCRIPTION OF THE PREFERRED EMBODIMENTS

The process of the present invention is particularly useful for producing highly fluorinated aliphatic compounds that are not easily prepared in typical fluorine for chlorine substitution reactions.

Thus, for example, in the catalyzed reaction of 1,1,1,3,3-pentachloropropane with hydrogen fluoride, fluorine substitution for chlorine is accompanied by large amounts of tar and byproducts. As a result, the desired pentafluoro compound is not formed in commercially acceptable yields.

Similarly, polychloro olefins such as 1,1,3,3-tetrachloroprop-1-ene with anhydrous hydrogen fluoride and a typical catalyst fail to yield the desired pentafluoropropane in acceptable yield due to extensive telomerization.

The process of the present invention overcomes these disadvantages by using as the starting material, a partially fluorinated, chloro- olefin of the formula

wherein c is 0 or the integer 1 and d is 0 or the integer 1 or 2. Numerous methods are available for the preparation of such starting material. For example see Laviron et al, U.S. Pat. No. 5,202,509.

It is preferred that the chlorofluoro olefin is prepared from the reaction of a polychloro compound of the formula

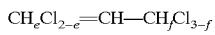

wherein e is 0 or the integer 1 and f is 0 or the integer 1 or 2 with hydrogen fluoride. The reaction is carried out for a time and at a temperature sufficient to produce the partially fluorinated, chloro olefin, also referred to herein as a "chlorofluoro olefin".

In the process to manufacture the chlorofluoro olefinic starting material, it is preferred that the polychloro compound is one where e is 0 or the integer 1 and f is the integer 1 or 2. Most preferably, e is 0 and f is 1, or e is 1 and f is 0.

At least three moles of hydrogen fluoride are required to produce the partially fluorinated, chloro olefin. However, an excess of hydrogen fluoride, preferably from about 2 to about 10 times the stoichiometric requirements are typically used in this reaction to facilitate the formation of the fluorochloro olefin.

The reaction according to the process of the present invention is carried out in the vapor phase. It is preferable to conduct the process in a continuous mode. As such, the process may be carried out over a catalytic bed that is fluidized or is static. can be in t he continuous or in a batch mode. Whether fluidized- or static bed-type reactions are employed, it is preferred as noted above, that the catalyst is present in the reaction vessel prior to the introduction of the chlorofluoro olefin and hydrogen fluoride.

A variety of catalysts are useful in carrying out the reaction of the chlorofluoro olefin and hydrogen fluoride in the vapor phase. To a large extent, many of these catalysts are equivalent and the choice of which one depends on cost and availability. The catalysts are metal halides, metal oxides or mixtures of such metal halides and/or metal oxides, which may be supported on alumina, chromia, or carbon.

The metals of these halides or oxides catalysts are selected from the group consisting of metals from Group IIIa, IIIb, IVa, IVb, Va, Vb, VIa, VIb, VIIb, or VIII of the Periodic Table of the Elements. Preferably the metal is a chloride or fluoride, most preferably a fluoride. It is preferably aluminum, antimony, bismuth, tin or a metal selected from the group consisting of from Group IVb, Vb, VIa, VIb, VIIb and VIII of the Periodic Table of the Elements. Preferably the catalyst is selected from the fluorides of antimony, tin, tantalum and titanium.

Especially preferred catalysts are the fluorides of aluminum, cobalt II or chromium III, fluorinated alumina, chromium fluoride, fluorinated chromia or antimony on chromia.

The halide or oxide of chromium III or the combination of antimony/titanium on carbon are particularly effective in carrying out the process of the present invention.

The process of the present invention is conducted in the vapor phase for a time sufficient to form the desired fluorinated aliphatic hydrocarbon. By suitable adjustment of pressure, times and temperatures for the process of the present invention typically are in the range of from about 100° C. to about 500° C. for about 1 second to about 25 seconds. Preferably the reaction temperature is from about 120° C. to about 475° C., most preferably 150° C. to about 425° C. Especially preferred reaction conditions are those at a temperature of from about 150–350° C. for from about 1 to about 2 seconds at a pressure of from about 100 to 200 psig.

The surface area of the catalysts used to effect the process of the present invention is lower then is typically expected for catalysts used in fluorination reactions. Thus, catalysts of use herein have a surface area of less than 100 square meters per gram($m^2$/g), preferably from about 20 to about 100 $m^2$/g, most preferably from about 40 to about 90 $m^2$/g. An especially preferred surface area for the catalysts of the present invention is about 75 $m^2$/g.

In the following examples, specific embodiments of the process of the present invention are disclosed. These are not included as limitations on the process but are for the purposes of illustration only. Unless indicated otherwise, temperatures are degrees Centigrade.

EXAMPLES

General Preparation of Catalyst

The catalyst bed is activated according to one of a number of methods already disclosed in the prior art. For example see WO 95/32935. In one of the embodiments of the process illustrated herein, a tubular reactor, constructed of hastelloy, Nickel, monel etc. (materials that can stand the rigors of the reaction components and conditions), is charged with ⅛" pellets of chromia. The filled tube is heated in a suitable furnace to a temperature sufficient for fluorination of the chromia to occur, e.g., 200–400° C. Anhydrous hydrofluoric acid is then allowed to flow thru the bed until adequate fluorination has occurred, typically from about 8 to about 24 hours. At this point the catalyst may be cooled and stored for future use. It may, however, be used immediately.

In anticipation of starting the feed of chlorofluoro olefin, a back pressure is allowed to build-up. Upon initiation of the feed, the back pressure controller is adjusted to compensate for generation of byproduct hydrogen chloride from the reaction.

Example 1

Preparation of 1,1,1,3,3-pentafluoropropane from 1-chloro-3,3,3,-trifluoro-1-propene A 24 inch×1 inch diameter carbon steel reactor was charged with fluorinated chromia and heated in a tube furnace to 350° C. An anhydrous hydrogen fluoride feed stream was initiated at 100 grams per hour (5 mole per hour). A feed of 1-chloro-3,3,3trifluoro-l-propene was then initiated at 65 grams per hour (0.5 mole per hour). The pressure of the system was maintained at 200 psig and the outflow stream collected over ice. The yield of 1,1,1,3,3-pentafluoropropane was 80% (by gas chromatograph).

Example 2

Preparation of 1,1,1,3,3-pentafluororpropane from 1-chloro-3,3,3-trifluropropene Chromia pellets (365 grams) were fluorinated as described in Example 1. The cooled pellets were then wetted with 108 grams of antimony trichloride. A 24 inch×1 inch diameter carbon steel reactor was charged with the antimony pentachloride-doped fluorinated chromia. The reactor was heated to 50° C. and an anhydrous hydrofluoric acid feed was initiated slowly. Over a period of several hours, the temperature was increased to 150° C. and the feed of hydrofluoric acid adjusted to 100 grams per hours (5.0 mol/hr). A feed of 1-chloro-3,3,3-trifluoropropene was then initiated at 65 grams per hour (0.5 mol/hr). The pressure of the system was maintained at 50 psig and the outflow stream collected on ice. The yield if 1,1,1,3,3-pentafluoropropane was 80% (by gas chromatograph).

Example 3

Preparation of 1,1,1,3,3-pentafluoropropane from 1-chloro-3,3,3-trifluoropropene Activated carbon (100 grams) was wetted with 98 grams of antimony pentachloride and 15.6 grams of titanium tetrachloride. A 12 inch×1 inch diameter carbon steel reactor was charged with the mixed metal halide-supported carbon. The reactor was heated to 50° C. and an anhydrous hydrofluoric acid feed was initiated slowly. Over a period of several hours, the temperature was increased to 200° C. and the feed of hydrofluoric acid adjusted to 100 grams per hours (2.0 mol/hr). A feed of 1-chloro-3,3,3-trifluoropropene was then initiated at 65 grams per hour (0.5 mol/hr). The pressure of the system was maintained at 100 psig and the outflow stream collected on ice. The yield if 1,1,1,3,3-pentafluoropropane was 43% (by gas chromatograph).

Example 4

Preparation of 1,1,1,3,3-pentafluoropropane from 1-chloro-3,3,3-trifluoropropene Antimony pentachloride, 260 grams, and 87 grams of aluminum chloride were charged into an autoclave. Hydrofluoric acid (1100 grams) was added with stirring and the reactor heated to 100° C. for 1 hour. The excess hydrofluoric acid was allowed to vent and the solid antimony/aluminum halide residue was pelletized. A 24 inch×1 inch diameter carbon steel reactor was charged with the pelletized catalyst. The reactor was then heated to 150° C. and an anhydrous hydrofluoric acid stream added at 100 grams per hour (5.0 mol/hr). A feed of 1-chloro-3,3,3-trifluoropropene was then initiated at 65 grams per hour (0.5 mol/hr). The pressure of the system was maintained at 50 psig and the outflow stream collected on ice. The yield if 1,1,1,3,3-pentafluoropropane was 40% (by gas chromatograph).

We claim:

1. A process for preparing a fluorinated aliphatic hydrocarbon of the formula $$CH_aF_{3-a}\text{---}CH_2\text{---}CH_bF_{3-b}$$

wherein a is 0 or the integer 1 or 2 and b is 0 or the integer 1, 2 or 3, comprising reacting in the vapor phase a chlorofluoro olefin of the formula $$CH_cCl_{2-c}\text{=}CH\text{---}CH_dF_{3-d}$$

wherein c is 0 or the integer 1 or 2, and d is 0 or the integer 1 or 2 with hydrogen fluoride and a catalytically effective amount of a metal oxide, metal halide or mixture thereof for a time sufficient to form said fluorinated aliphatic hydrocarbon.

2. The process according to claim 1 wherein a and c are the integer 1 and b and d are 0.

3. The process according to claim 1 wherein a and c are the integer 1 and b and d are 0.

4. The process according to claim 1 wherein a,b,c and d are 0.

5. The process according to claim 1 wherein said temperature of is from about 225° C. to about 500° C.

6. The process according to claim 1 wherein the metal in said metal halide, metal oxide or mixture thereof is selected from the group consisting of a metal from Group IIIa, IIIb, IVa, IVb, Va, Vb, VIa, VIb, VIIb and VIII of the Periodic Table of the Elements.

7. The process according to claim 6 wherein the metal in said metal halide, metal oxide or mixture thereof is antimony, bismuth, chromium, tin, or is selected from the group consisting of the metals of Group IVb, Vb, VIa, VIb, VIIb and VIII of the Periodic Table of the Elements.

8. The process according to claim 7 wherein said metal halide, metal oxide or mixture thereof is supported on alumina, chromia, or carbon.

9. The process according to claim 1 wherein said metal halide, metal oxide or mixture thereof is aluminum fluoride, cobalt II fluoride, chromium III chloride, fluorinated alumina or fluorinated chromia.

10. A process for preparing 1,1,1,3,3-pentafluoropropane which comprises reacting in the vapor phase a chlorofluoro olefin of the formula $$CHCl\text{=}CH\text{---}CHF_2$$

with hydrogen fluoride and a catalytically effective amount of a fluidized bed of a halide or oxide of chromium for a time sufficient to form said 1,1,1,3,3-pentafluoropropane.

* * * * *